United States Patent
Burrows (10) Patent No.: US 9,831,639 B2
(45) Date of Patent: Nov. 28, 2017

(54) CONCURRENT METHOD FOR RESONANT FREQUENCY DETECTION IN CORONA IGNITION SYSTEMS

(71) Applicant: Federal-Mogul Ignition Company, Southfield, MI (US)

(72) Inventor: John Antony Burrows, Timperly (GB)

(73) Assignee: Federal-Mogul Ignition Company, Southfield, MI (US)

( * ) Notice: Subject to any disclaimer, the term of this patent is extended or adjusted under 35 U.S.C. 154(b) by 347 days.

(21) Appl. No.: 14/568,266

(22) Filed: Dec. 12, 2014

(65) Prior Publication Data

US 2015/0168258 A1    Jun. 18, 2015

Related U.S. Application Data

(60) Provisional application No. 61/915,088, filed on Dec. 12, 2013, provisional application No. 61/931,131,
(Continued)

(51) Int. Cl.
*H01T 19/00* (2006.01)
*G01M 15/02* (2006.01)
(Continued)

(52) U.S. Cl.
CPC .............. *H01T 19/00* (2013.01); *F02P 23/04* (2013.01); *G01M 15/02* (2013.01); *G01N 27/02* (2013.01);
(Continued)

(58) Field of Classification Search
CPC ........ G01R 23/00; G01R 23/02; G01R 27/32; A61B 2560/0219; F02P 23/04; G01N 27/02; G01M 15/02
(Continued)

(56) References Cited

U.S. PATENT DOCUMENTS

| 1,022,584 A | * | 4/1912 | Fessenden | ............. | G01R 23/04 |
| | | | | | 324/76.51 |
| 2,598,301 A | * | 5/1952 | Rajchman | ............. | G01R 23/00 |
| | | | | | 313/103 R |

(Continued)

FOREIGN PATENT DOCUMENTS

| CN | 101351638 A | 1/2009 |
| CN | 101743395 A | 6/2010 |

(Continued)

OTHER PUBLICATIONS

International Search Report, dated Mar. 25, 2015 (PCT/US2014/069952).

(Continued)

*Primary Examiner* — Jermele M Hollington
*Assistant Examiner* — Christopher McAndrew
(74) *Attorney, Agent, or Firm* — Robert L. Stearns; Dickinson Wright, PLLC (57) ABSTRACT

A system and method for detecting resonant frequency of a corona igniter concurrent with operation of the corona igniter is provided. The method includes providing a plurality of pulses of energy to the corona igniter, each having a pulse duration and spaced from one another by a deadtime duration during which no energy is provided to the corona igniter. Each pulse duration is ceased before current flowing in the corona igniter crosses zero, and each zero crossing of the current occurs during one of the deadtime durations. The next pulse of energy is provided to the corona igniter in response to the zero crossing of the current. A resonant frequency value is then obtained based on a sum of the pulse and deadtime durations of two consecutive cycles, or the time between zero crossings. The resonant frequency values become more accurate over time, and the drive frequency is adjusted accordingly.

13 Claims, 5 Drawing Sheets

Related U.S. Application Data filed on Jan. 24, 2014, provisional application No. 61/950,991, filed on Mar. 11, 2014, provisional application No. 62/072,530, filed on Oct. 30, 2014, provisional application No. 62/090,096, filed on Dec. 10, 2014.

(51) Int. Cl.
| | | |
|---|---|---|
| G01N 27/02 | (2006.01) | |
| F02P 23/04 | (2006.01) | |
| H01T 15/00 | (2006.01) | |
| H02M 3/00 | (2006.01) | |
| F02P 3/04 | (2006.01) | |
| F02P 5/15 | (2006.01) | |
| F02P 17/00 | (2006.01) | |

(52) U.S. Cl.
CPC .............. H01T 15/00 (2013.01); H02M 3/00 (2013.01); *F02N 2300/2011* (2013.01); *F02P 3/0407* (2013.01); *F02P 5/1502* (2013.01); *F02P 17/00* (2013.01)

(58) Field of Classification Search
USPC ...................................................... 324/76.51
See application file for complete search history.

(56) References Cited

U.S. PATENT DOCUMENTS

| | | | | |
|---|---|---|---|---|
| 2,600,186 | A * | 6/1952 | Banos, Jr. | H01P 7/06 324/76.51 |
| 2,660,711 | A * | 11/1953 | Garbuny | H01P 7/06 324/76.51 |
| 2,967,996 | A * | 1/1961 | Bradford | G01R 31/255 324/409 |
| 3,034,064 | A * | 5/1962 | Broussand | G01R 23/04 315/39.3 |
| 3,085,199 | A * | 4/1963 | Foss | H01P 7/06 116/255 |
| 3,090,018 | A * | 5/1963 | Foss | H01P 7/06 324/76.51 |
| 3,833,492 | A * | 9/1974 | Bollyky | C01B 13/11 204/176 |
| 3,883,413 | A * | 5/1975 | Douglas-Hamilton | C01B 13/11 204/176 |
| 4,208,992 | A | 6/1980 | Polo | |
| 4,495,043 | A * | 1/1985 | Marets | C01B 13/115 204/176 |
| 4,629,977 | A * | 12/1986 | English | G01H 13/00 324/603 |
| 4,682,266 | A * | 7/1987 | Huynh | C01B 13/115 323/903 |
| 5,130,003 | A * | 7/1992 | Conrad | C01B 13/115 204/176 |
| 5,149,940 | A | 9/1992 | Davis et al. | |
| 5,179,928 | A | 1/1993 | Cour et al. | |
| 5,269,893 | A * | 12/1993 | Conrad | C01B 13/115 204/176 |
| 5,361,737 | A | 11/1994 | Smith et al. | |
| 5,486,993 | A * | 1/1996 | Sakurai | H02M 7/53871 363/137 |
| 5,513,618 | A | 5/1996 | Rich et al. | |
| 5,568,801 | A | 10/1996 | Paterson et al. | |
| 6,758,199 | B2 | 7/2004 | Masters et al. | |
| 6,883,507 | B2 | 4/2005 | Freen | |
| 7,956,543 | B2 | 6/2011 | Agneray et al. | |
| 7,974,068 | B2 | 7/2011 | Agneray et al. | |
| 8,342,147 | B2 | 1/2013 | Nouvel et al. | |
| 8,547,020 | B2 | 10/2013 | Barroso et al. | |
| 8,552,651 | B2 | 10/2013 | Sugino et al. | |
| 8,567,372 | B2 | 10/2013 | Visser et al. | |
| 8,578,902 | B2 | 11/2013 | Permuy et al. | |
| 8,800,539 | B2 | 8/2014 | Toedter et al. | |
| 8,869,765 | B2 | 10/2014 | Braeuchle | |
| 8,973,561 | B2 * | 3/2015 | Ruan | F02P 23/04 123/143 B |
| 9,181,920 | B2 * | 11/2015 | Burrows | F02P 23/04 |
| 9,318,881 | B2 * | 4/2016 | Burrows | H01T 19/00 |
| 9,466,953 | B2 * | 10/2016 | Burrows | F02P 23/04 |
| 9,525,274 | B2 * | 12/2016 | Burrows | H01T 19/00 |
| 2003/0057935 | A1 * | 3/2003 | Yoshida | G11B 21/10 324/76.51 |
| 2004/0129241 | A1 | 7/2004 | Freen | |
| 2005/0016456 | A1 * | 1/2005 | Taguchi | H05H 1/2406 118/723 E |
| 2009/0122583 | A1 | 5/2009 | Gelerter | |
| 2009/0194051 | A1 | 8/2009 | Smith et al. | |
| 2009/0229581 | A1 | 9/2009 | Ikeda | |
| 2010/0083942 | A1 * | 4/2010 | Lykowski | F02B 19/12 123/647 |
| 2010/0116257 | A1 | 5/2010 | Agneray et al. | |
| 2010/0229639 | A1 | 9/2010 | Agneray et al. | |
| 2010/0251995 | A1 | 10/2010 | Nouvel et al. | |
| 2010/0282198 | A1 | 11/2010 | Hampton et al. | |
| 2010/0313841 | A1 | 12/2010 | Agneray et al. | |
| 2011/0114071 | A1 | 5/2011 | Freen | |
| 2011/0146607 | A1 | 6/2011 | Smith et al. | |
| 2011/0175691 | A1 | 7/2011 | Smith et al. | |
| 2011/0253114 | A1 | 10/2011 | Schremmer | |
| 2011/0297132 | A1 | 12/2011 | Schremmer et al. | |
| 2011/0305998 | A1 | 12/2011 | Toedter et al. | |
| 2012/0055430 | A1 | 3/2012 | Braeuchle | |
| 2012/0055455 | A1 * | 3/2012 | Ruan | F02P 23/04 123/608 |
| 2012/0063054 | A1 * | 3/2012 | Burrows | F23Q 3/00 361/256 |
| 2012/0145136 | A1 | 6/2012 | Burrows et al. | |
| 2012/0180742 | A1 | 7/2012 | Burrows | |
| 2012/0249006 | A1 | 10/2012 | Burrows | |
| 2012/0249163 | A1 | 10/2012 | Burrows | |
| 2013/0208393 | A1 | 8/2013 | Hampton et al. | |
| 2013/0300474 | A1 | 11/2013 | Chang et al. | |
| 2013/0308347 | A1 | 11/2013 | Sato et al. | |
| 2014/0174392 | A1 * | 6/2014 | Burrows | F02P 23/04 123/143 B |
| 2014/0226252 | A1 | 8/2014 | Freen | |
| 2015/0168258 | A1 * | 6/2015 | Burrows | G01M 15/02 73/114.62 |
| 2015/0171601 | A1 * | 6/2015 | Burrows | G01M 15/02 361/263 |
| 2015/0171602 | A1 * | 6/2015 | Burrows | G01M 15/02 361/230 |
| 2016/0222940 | A1 * | 8/2016 | Burrows | F02P 23/04 |
| 2016/0344166 | A1 * | 11/2016 | Hampton | H01T 19/00 |

FOREIGN PATENT DOCUMENTS

| | | |
|---|---|---|
| CN | 102562412 A | 7/2012 |
| CN | 102804527 A | 11/2012 |
| CN | 103597202 A | 2/2014 |
| DE | 19747701 A1 | 5/1999 |
| DE | 102005036968 A1 | 2/2007 |
| DE | 102010062304 A1 | 6/2012 |
| DE | 102010062305 A1 | 6/2012 |
| WO | 2010011838 A1 | 1/2010 |
| WO | 2012138674 A1 | 10/2012 |

OTHER PUBLICATIONS

International Search Report, dated Mar. 25, 2015 (PCT/US2014/069947).

International Search Report, dated Mar. 25, 2015 (PCT/US2014/069958).

International Search Report, dated Mar. 25, 2015 (PCT/US2014/069974).

* cited by examiner

CONCURRENT METHOD FOR RESONANT FREQUENCY DETECTION IN CORONA IGNITION SYSTEMS

CROSS-REFERENCE TO RELATED APPLICATIONS

This U.S. patent application claims the benefit of U.S. provisional patent application No. 61/915,088, filed Dec. 12, 2013; U.S. provisional patent application No. 61/931,131, filed Jan. 24, 2014; U.S. provisional patent application No. 61/950,991, filed Mar. 11, 2014; U.S. provisional patent application No. 62/072,530, filed Oct. 30, 2014; and U.S. provisional patent application No. 62/090,096, filed Dec. 10, 2014, the entire contents of each being incorporated herein by reference in their entirety.

BACKGROUND OF THE INVENTION

1. Field of the Invention

This invention relates generally to a corona discharge ignition system, and more particularly to methods for controlling energy supplied to the corona igniter system.

2. Related Art

Corona discharge ignition systems provide an alternating voltage and current, reversing high and low potential electrodes in rapid succession which enhances the formation of corona discharge and minimizes the opportunity for arc formation. The system includes a corona igniter with a central electrode charged to a high radio frequency voltage potential and creating a strong radio frequency electric field in a combustion chamber. The electric field causes a portion of a mixture of fuel and air in the combustion chamber to ionize and begin dielectric breakdown, facilitating combustion of the fuel-air mixture, which is referred to as an ignition event. The electric field is preferably controlled so that the fuel-air mixture maintains dielectric properties and corona discharge occurs, also referred to as a non-thermal plasma. The ionized portion of the fuel-air mixture forms a flame front which then becomes self-sustaining and combusts the remaining portion of the fuel-air mixture. Preferably, the electric field is controlled so that the fuel-air mixture does not lose all dielectric properties, which would create thermal plasma and an electric arc between the electrode and grounded cylinder walls, piston, metal shell, or other portion of the igniter. An example of a corona discharge ignition system is disclosed in U.S. Pat. No. 6,883,507 to Freen.

In addition, the corona discharge ignition system is preferably controlled so that energy is provided to the corona igniter at a drive frequency equal or close to the resonant frequency of the corona igniter. This provides a voltage amplification leading to robust corona discharge in the combustion chamber. Accurately detecting the resonant frequency of the corona igniter is necessary in order to achieve this high level of control. However, accurate detection of the resonant frequency it is difficult to achieve, especially at a wide range of frequencies. Changes in the resonant frequency during operation, for example due to arcing events, also make it difficult to accurately detect the resonant frequency.

SUMMARY OF THE INVENTION

One aspect of the invention provides an improved method for detecting the resonant frequency of a corona igniter concurrent with operation of the corona igniter in a corona ignition system. The method includes providing a first pulse of energy to a corona igniter at a positive voltage for a first pulse duration causing causes current to flow in the corona igniter; and ceasing the first pulse duration before the current flowing in the corona igniter crosses through zero. A first deadtime duration occurs immediately upon ceasing the first pulse duration, and no energy is provided to the corona igniter during the first deadtime duration. The method further includes detecting when the current flowing in the corona igniter crosses through zero during the first deadtime duration; and providing a second pulse of energy to the corona igniter at a negative voltage for a second pulse duration in response to the zero crossing of the current to cease the first deadtime duration. The method then includes ceasing the second pulse duration before the current crosses through zero. A second deadtime duration occurs immediately upon ceasing the second pulse duration, and no energy is provided to the corona igniter during the second deadtime duration. The method further includes detecting when the current flowing in the corona igniter crosses through zero during the second deadtime duration; and providing a third pulse of energy to the corona igniter at a positive voltage in response to the zero crossing of the current to cease the second deadtime duration. The method then includes obtaining a first resonant frequency value based on a sum of the first pulse duration, the first deadtime duration, the second pulse duration, and the second deadtime duration.

Another aspect of the invention provides a method for detecting the resonant frequency of a corona igniter in a corona ignition system, comprising the steps of: providing a first pulse of energy to a corona igniter at a positive voltage causing causes current to flow in the corona igniter; ceasing the first pulse before the current flowing in the corona igniter crosses through zero and providing no energy to the corona igniter for a first deadtime duration immediately upon ceasing the first pulse of energy; and obtaining a first zero crossing duration, wherein the first zero crossing duration begins at the start of the first pulse of energy and ends at the first zero crossing. The method further includes obtaining a first resonant frequency value by doubling the first zero crossing duration.

Another aspect of the invention provides a method for detecting the resonant frequency of a corona igniter in a corona ignition system, comprising the steps of: providing a first pulse of energy to a corona igniter at a positive voltage causing causes current to flow in the corona igniter; ceasing the first pulse before the current flowing in the corona igniter crosses through zero and providing no energy to the corona igniter for a first deadtime duration immediately upon ceasing the first pulse of energy; and obtaining a first zero crossing duration, wherein the first zero crossing duration begins at the start of the first pulse of energy and ends when the current flowing in the corona igniter crosses through zero during the first deadtime duration. The method next includes providing a second pulse of energy to the corona igniter at a negative voltage in response to the first zero crossing of the current to cease the first deadtime duration; ceasing the second pulse of energy before the current crosses through zero and providing no energy to the corona igniter for a second deadtime duration immediately upon ceasing the second pulse of energy; and obtaining a second zero crossing duration, wherein the second zero crossing duration begins at the first zero crossing and ends when the current flowing in the corona igniter crosses through zero during the second deadtime duration. The method then includes obtaining a first resonant frequency value based on a sum of the first zero crossing duration and the second zero crossing duration.

Another aspect of the invention provides a system for detecting the resonant frequency of a corona igniter. The system includes a first switch providing a first pulse of energy from an energy supply to a corona igniter at a positive voltage for a first pulse duration causing current to flow in the corona igniter. The first switch ceases the first pulse duration before the current in the corona igniter crosses through zero. No energy is provided to the corona igniter for a first deadtime duration which occurs immediately upon ceasing the first pulse duration. A frequency detector detects when the current flowing in the corona igniter crosses through zero during the first deadtime duration and initiates a drive signal to provide a second pulse of energy to the corona igniter in response to the zero crossing of the current. A second switch receives the drive signal and provides the second pulse of energy from the energy supply to the corona igniter at a negative voltage for a second pulse duration to cease the first deadtime duration. The second switch ceases the second pulse duration before the current flowing in the corona igniter crosses through zero. No energy is provided to the corona igniter for a second deadtime duration which occurs immediately upon ceasing the second pulse duration. The frequency detector detects when the current flowing in the corona igniter crosses through zero during the second deadtime duration and initiates a drive signal to provide a third pulse of energy to the corona igniter in response to the zero crossing of the current. The first switch receives the drive signal and provides the third pulse of energy from the energy supply to the corona igniter at a positive voltage to cease the second deadtime duration. The frequency detector then obtains a first resonant frequency value based on a sum of the first pulse duration, the first deadtime duration, the second pulse duration, and the second deadtime duration.

Yet another aspect of the invention provides a system for detecting the resonant frequency of a corona igniter in a corona ignition system, comprising a first switch and a frequency detector. The first switch provides a first pulse of energy from an energy supply to a corona igniter at a positive voltage causing current to flow in the corona igniter The first switch then ceasing the first pulse of energy before the current in the corona igniter crosses through zero and provides no energy to the corona igniter for a first deadtime duration immediately upon ceasing the first pulse of energy. The frequency detector then obtains a resonant frequency value by doubling a first zero crossing duration, wherein the first zero crossing duration begins at the start of the first pulse of energy and ends at the first zero crossing.

Another aspect of the invention provides a system for detecting the resonant frequency of a corona igniter in a corona ignition system, comprising a first switch, a second switch, and a frequency detector. The first switch provides a first pulse of energy from an energy supply to a corona igniter at a positive voltage causing current to flow in the corona igniter. The first switch ceases the first pulse duration before the current in the corona igniter crosses through zero and provides no energy to the corona igniter for a first deadtime duration immediately upon ceasing the first pulse of energy. The frequency detector detects when the current flowing in the corona igniter crosses through zero during the first deadtime duration and initiates a drive signal to provide a second pulse of energy to the corona igniter in response to the first zero crossing of the current. The frequency detector obtains a first zero crossing duration, wherein the first zero crossing duration begins at the start of the first pulse of energy and ends at the first zero crossing. The second switch receives the drive signal and provides the second pulse of energy from the energy supply to the corona igniter at a negative voltage to cease the first deadtime duration. The second switch ceases the second pulse duration before the current flowing in the corona igniter crosses through zero and provides no energy to the corona igniter for a second deadtime duration immediately upon ceasing the second pulse of energy. The frequency detector detects when the current flowing in the corona igniter crosses through zero during the second deadtime duration. The frequency detector obtains a second zero crossing duration, wherein the second zero crossing duration begins at the first zero crossing and ends at the second zero crossing. The frequency detector obtains a first resonant frequency value based on a sum of the first zero crossing duration and the second zero crossing duration.

The system and method provide numerous advantages. First, the resonant frequency values obtained become more accurate over time, and are equal to, or very close to, the actual resonant frequency of the corona igniter. In addition, the resonant frequency values are obtained while energy is being supplied to the corona igniter, and typically while the corona igniter provides corona discharge. Thus, additional power phase or measurement periods are not required. Furthermore, the drive frequency of the energy provided to the corona igniter can be immediately adjusted concurrent with operation of the corona igniter, or prior to a future corona event, to match the detected resonant frequency value, for example in response to changes caused by arcing events or other conditions.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION

The present invention provides an improved system 20 and method for detecting the resonant frequency of a corona igniter 22 concurrent with operation of the corona igniter 22. The resonant frequency values obtained using the method are equal to, or very close to, the actual resonant frequency of the corona igniter 22. The drive frequency of the energy provided to the corona igniter 22 can be adjusted to match the detected resonant frequency value while the energy is being supplied to the corona igniter 22 and while the corona igniter 22 provides corona discharge 26. In addition, immediate adjustments to the drive frequency can be made during operation of the corona igniter 22 based on the detected resonant frequency value, for example in response to changes caused by arcing events or other conditions.

Figure 1:
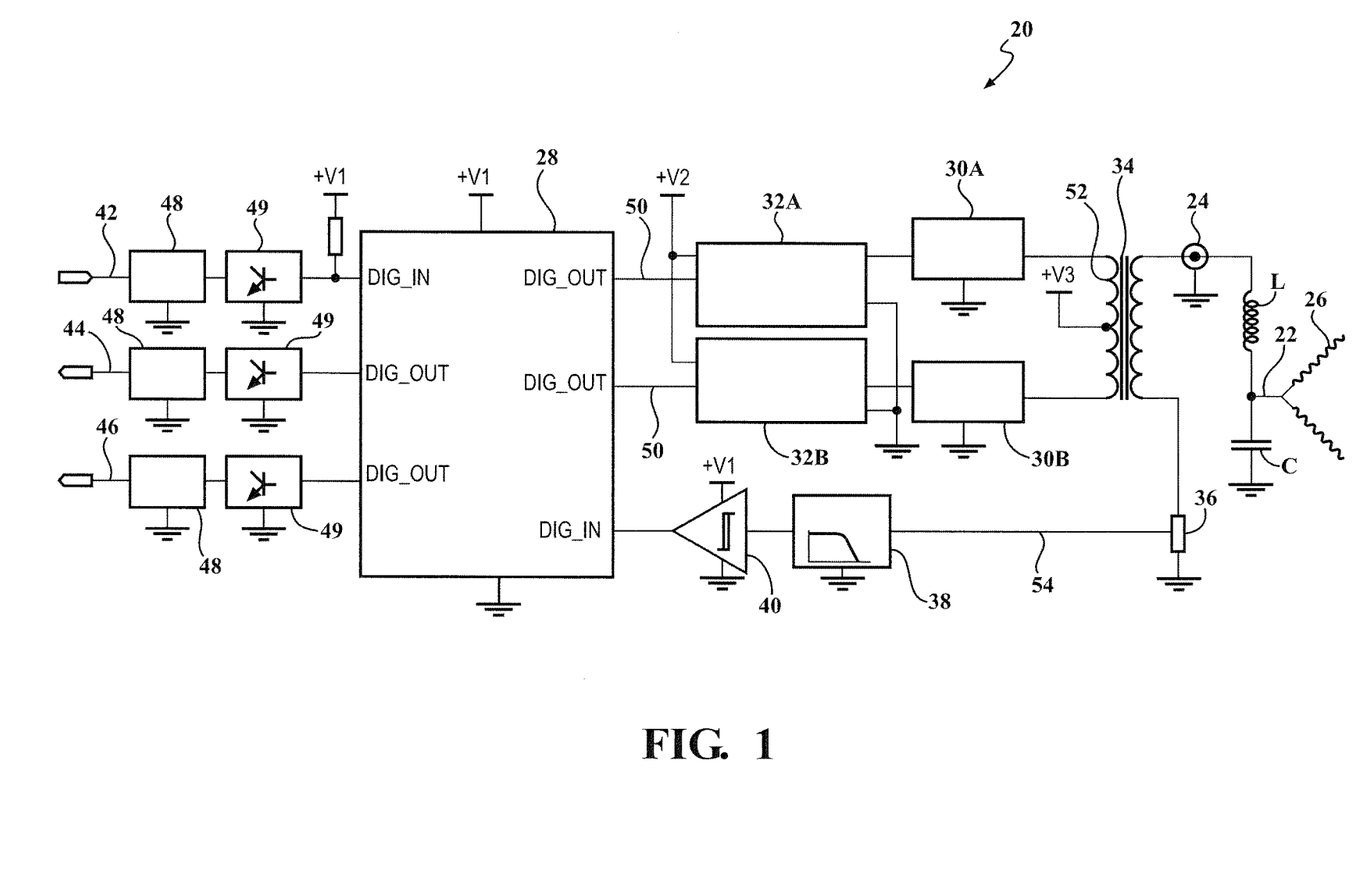
FIG. 1 is a block diagram of a corona discharge ignition system according to a first exemplary embodiment of the invention.
Figure 2:
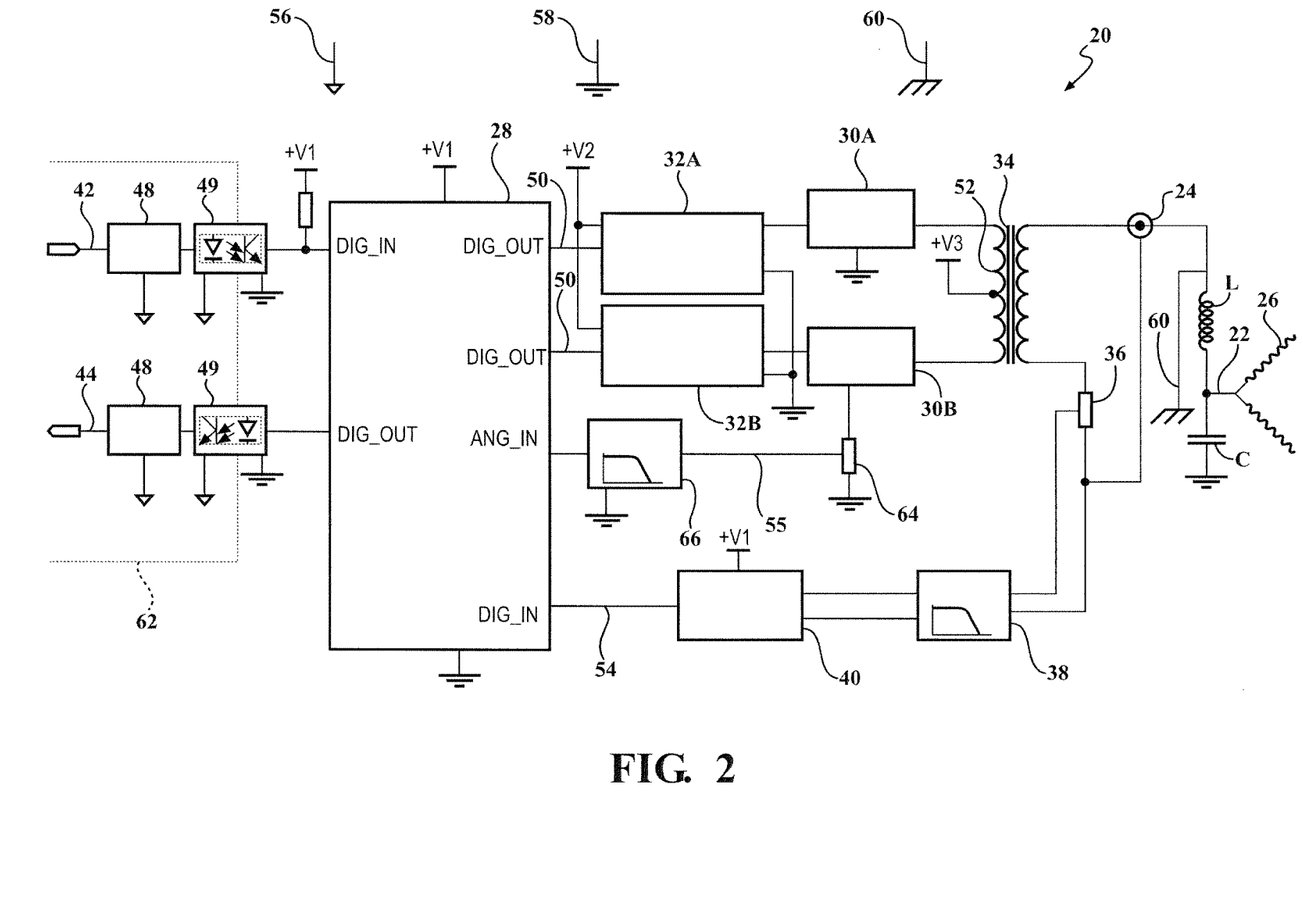
FIG. 2 is a block diagram of a corona discharge ignition system according to a second exemplary embodiment of the invention.
Figure 3:
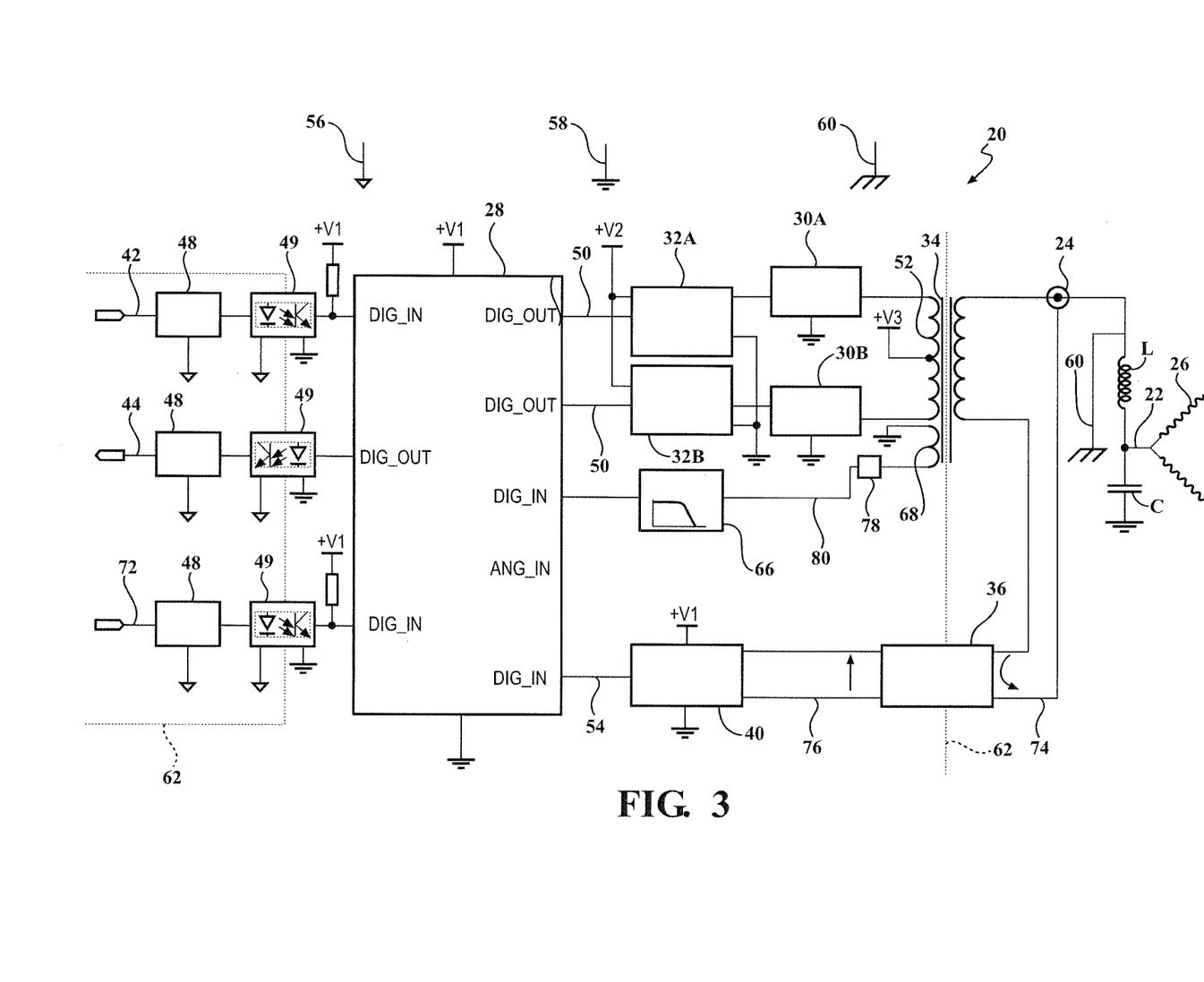
FIG. 3 is a block diagram of a corona discharge ignition system according to a third exemplary embodiment of the invention.

Exemplary embodiments of the system 20 capable of implementing the improved resonant frequency detection are shown in FIGS. 1-3. These systems 20 are also described in related U.S. patent application Ser. Nos. 14/568,219, 14/568,330, and 14/568,438, which are incorporated herein by reference. In each embodiment, the system 20 includes the corona igniter 22 coupled to an induction coil L, which are together referred to as the load operating at a resonant frequency. This resonant frequency is referred to herein as "the resonant frequency of the corona igniter 22." The corona igniter 22 receives energy at a drive frequency and voltage level causing current to flow in the corona igniter 22. This current and voltage can be measured at an output 24 of the corona igniter 22. During operation in an internal combustion engine, the corona igniter 22 preferably forms a high radio frequency electric field at a firing end, referred to as corona discharge 26, to ignite a mixture of fuel and air in a combustion chamber of the engine.

The system 20 also includes the controller 28 and a pair of switches 30A, 30B that control the drive frequency provided to the corona igniter 22, and the capacitance/inductance circuit of the system 20, so that the drive frequency is maintained at or close to the resonant frequency of the corona igniter 22. Operating the system 20 such that the drive frequency is equal to the resonant frequency provides voltage amplification leading to robust corona discharge 26 in the combustion chamber.

The controller 28 of the exemplary embodiments activates one of the switches 30A or 30B at predetermined times to achieve the desired drive frequency. When one of the switches 30A or 30B is active, energy can flow from the power supply V3 through the active switch 30A or 30B to the corona igniter 22. When the switches 30A, 30B are not active, energy cannot flow through to the corona igniter 22. Switch 30A is referred to as a first switch, and switch 30B is referred to as a second switch, but the switch 30B could alternatively be referred to as the first switch, and the switch 30A could be referred to as the second switch. In each case, only one of the switches 30A or 30B is active and providing energy to the corona igniter 22 at any given time during operation of the corona ignition system 20. Thus, the controller 28 deactivates the first switch 30A before activating the second switch 30B, and vice versa, so that the two switches 30A, 30B are not active at the same time. Preferably, activation of the switches 30A, 30B is synchronized with the resonant frequency of the corona igniter 22. For example, in one embodiment, the first switch 30A is active and thus provides energy to the corona igniter 22 whenever the current at the output 24 is positive, and the second switch 30B is active and thus provides energy to the corona igniter 22 whenever the current at the output 24 is negative. The system 20 also includes a frequency detector for detecting the resonant frequency of the corona igniter 22. The frequency detector is typically provided by a combination of components working together, for example the controller 28 working in combination with a current sensor 36, or other components of the system 20.

The method of detecting the resonant frequency is conducted concurrent with operation of the corona igniter 22 in an internal combustion engine. This case, the method is conducted while energy is provided to the corona igniter 22 and typically while the corona igniter 22 provides corona discharge 26. However, the method can also be conducted at a reduced duty cycle, wherein the energy provided to the corona igniter 22 is at lower level so that the corona discharge 26 is not created. The method could also being at the reduced duty cycle, and the duty cycle can be increased over time.

Figure 4:
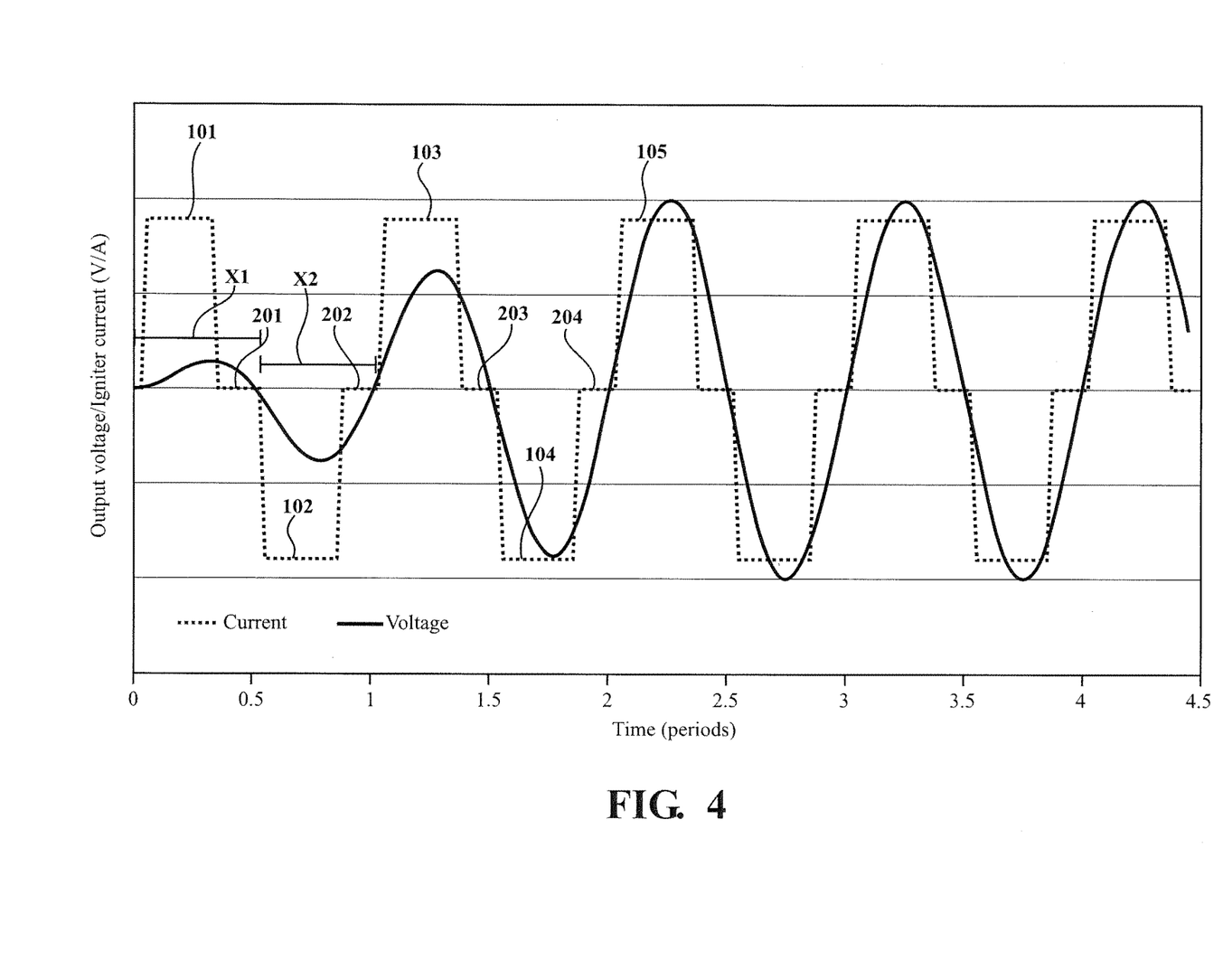
FIG. 4 is a graph illustrating current flowing in the corona igniter and voltage provided to the corona igniter at the beginning of a corona event.
Figure 5:
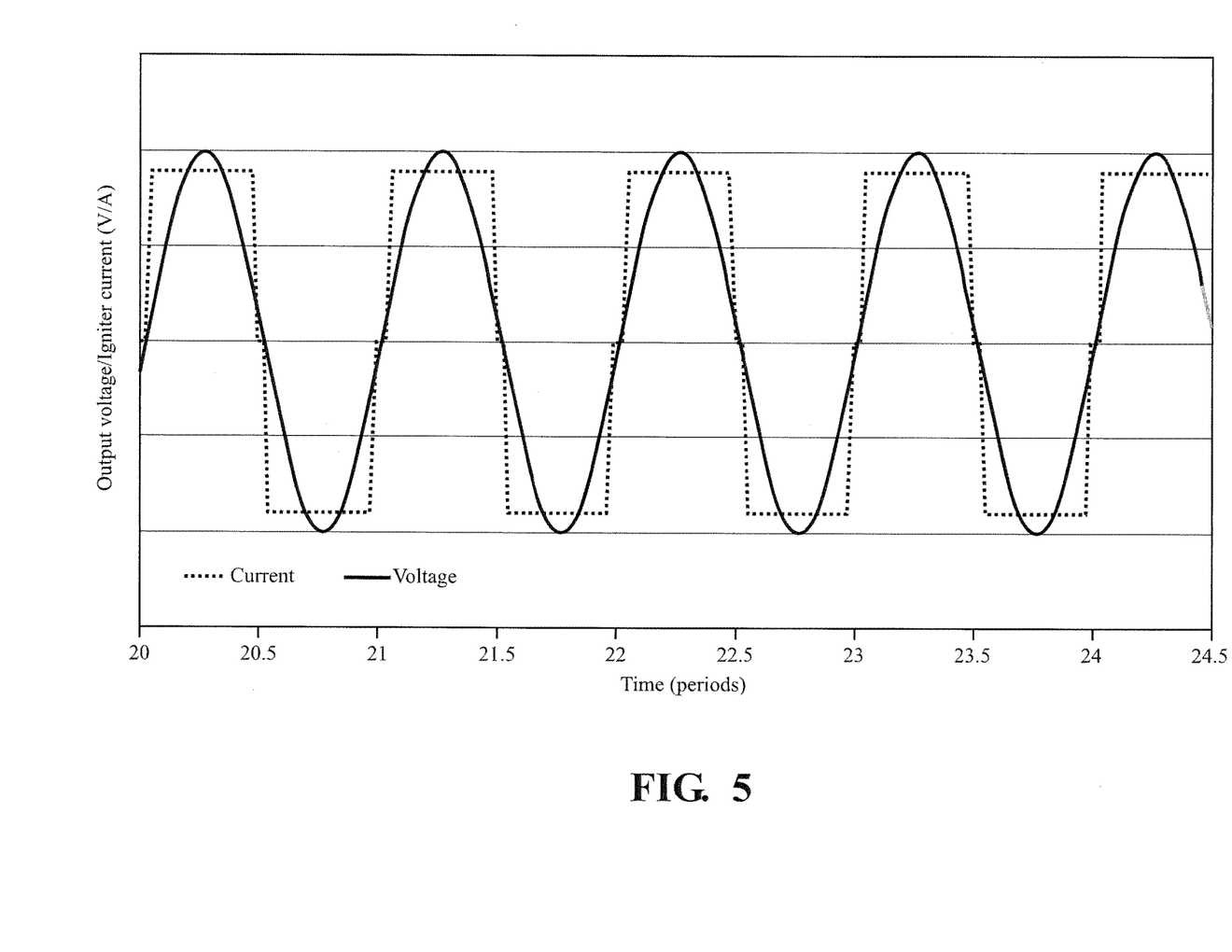
FIG. 5 shows the current flowing in the corona igniter and the voltage provided to the corona igniter after 20 cycles in the corona event of FIG. 4.

FIGS. 4 and 5 provide an example of the voltage provided to the corona igniter 22 and the current flowing in the corona igniter 22 while implementing the method of the present invention. FIG. 4 shows the current and voltage at the beginning of a corona event, and FIG. 5 shows the current and voltage after 20 cycles of the same corona event. The "corona event" is a period of time during energy is provided to the corona igniter 22 and the corona igniter 22 provides a corona discharge 26. These current and voltage levels are used to detect the resonant frequency of the corona igniter 22, as will be discussed further below.

In general, the method includes employing the first switch 30A to provide a first pulse of energy from an energy supply, for example V3, to the corona igniter 22. The first pulse of energy is provided at a positive voltage for a first pulse duration 101 causing a positive current to flow in the corona igniter 22. The first switch 30A then ceases the first pulse duration 101 before the current in the corona igniter 22 crosses through zero, as shown in FIG. 4. The controller 28 typically sets the length of the first pulse duration 101 based on any delays of components of the system 20, so that the first pulse duration 101 ends before the current flowing in the corona igniter 22 crosses through zero.

A first deadtime duration 201 then occurs immediately upon ceasing the first pulse duration 101. No energy is provided from the energy supply V3, or from any other type of energy source, to the corona igniter 22 during the first deadtime duration 201, and the voltage level is at zero during the first deadtime duration 201, as shown in FIG. 4. Since the energy is powered off during the first deadtime duration 201, there are no problems associated with noise in the corona circuit due to switching.

During the first deadtime duration 201, the frequency detector, such as a combination of the controller 28 and current sensor 36, detects when the current flowing in the corona igniter 22 crosses through zero. The current crosses zero only once during the first deadtime duration 201. In one embodiment, the current sensor 36 obtains the current flowing in the corona igniter 22 from the output 24 and determines the zero crossings of the current. This zero crossing measurement is typically conveyed from the current sensor 36 to the controller 28 in an output signal 54.

The controller 28 receives the output signal 54, and in response to the zero crossing of the current, the controller 28 initiates a drive signal 50 to provide a second pulse of energy to the corona igniter 22. The second switch 30B receives the drive signal 50 and provides the second pulse of energy from the energy supply V3 to the corona igniter 22 at a negative voltage for a second pulse duration 102 to cease the first deadtime duration 201. The second switch 30B ceases the second pulse duration 102 before the negative current flowing in the corona igniter 22 crosses through zero, as shown in FIG. 4. The controller 28 can also set the length of the second pulse duration 102 based on any delays of components of the system 20, so that the second pulse duration 102 ends before the current flowing in the corona igniter 22 crosses through zero.

A second deadtime duration 202 then occurs immediately upon ceasing the second pulse duration 102. No energy is provided from the energy supply V3, or from any other energy source, to the corona igniter 22 during the second deadtime duration 202, and the voltage level during the second deadtime duration 202 is at zero, as shown in FIG. 4. The second pulse duration 102 is greater than the first pulse duration 101, and the second deadtime duration 202 is less than the first deadtime duration 201.

During the second deadtime duration 202, the frequency detector again detects when the current flowing in the corona igniter 22 crosses through zero, in the same manner as during the first deadtime duration 201. The current crosses zero only once during the second deadtime duration 202. In response to the zero crossing of the current, the frequency detector, typically the controller 28, initiates another drive signal 50 to provide a third pulse of energy to the corona igniter 22. The first switch 30A receives the drive signal 50 and provides the third pulse of energy from the energy supply V3 to the corona igniter 22 at a positive voltage to cease the second deadtime duration 202.

After the second deadtime duration 202, the frequency detector obtains a first resonant frequency value based on a sum of the first pulse duration 101, the first deadtime duration 201, the second pulse duration 102, and the second deadtime duration 202. Typically, the controller 28 receives information about the current and voltage from other components of the system, and then uses that information to determine the pulse durations 101, 102 and deadtime durations 201, 202. The controller 28 then uses the sum of those durations 101, 102, 201, 202 to determine the first resonant frequency value. Various different methods can be used to determine the first resonant frequency value based on the sum, such as algorithms performed by software of the controller 28. For example, the step of obtaining the first resonant frequency value can include dividing the sum in half to determine the duration of one half cycle of the resonant frequency. As indicated above, the gathering of information and evaluation conducted by the controller 28 to obtain the first resonant frequency value can be conducted during the corona event, while providing the energy to the corona igniter 22.

In another embodiment, the frequency detector, such as the current sensor 36 and the controller 28, determines the first resonant frequency value by obtaining the time between adjacent zero crossings, which can include the time between the start of the first pulse of energy and the first zero crossing, or the time between two consecutive zero crossings. For example, the controller 28 can obtain the first resonant frequency value by doubling a first zero crossing duration X1. As shown in FIG. 4, the first zero crossing duration X1 begins at the start of a pulse of energy and ends at a first zero crossing. The first zero crossing could be at startup, as shown in FIG. 4, but could alternatively be the time between two later zero crossings.

The controller 28 could alternatively obtain the first resonant frequency value based on the time between three consecutive zero crossings, which could be the first three consecutive zero crossings, as shown in FIG. 4, or three later zero crossings. In this embodiment, the controller 28 obtains the first zero crossing duration X1 and a second zero crossing duration X2, wherein the second zero crossing duration X2 begins at the first zero crossing and ends at the second zero crossing. The controller 28 obtains a first resonant frequency value based on a sum of the first zero crossing duration X1 and the second zero crossing duration X2.

After the first resonant frequency value is obtained, the controller 28 can adjust the drive frequency of the energy provided to the corona igniter 22 to equal the obtained first resonant frequency value, concurrently with operation of the corona igniter 22. The controller 28 typically instructs the switches 30A, 30B to provide the energy from the energy supply V3 to the corona igniter 22 at the first resonant frequency value while the corona igniter 22 continues to provide the corona discharge 26. Determining the first resonant frequency value and adjusting the drive frequency to match the obtained first resonant frequency value can all occur in the same corona event.

The above steps are typically repeated over several cycles or time periods, as shown in FIGS. 4 and 5, to obtain additional resonant frequency values, wherein each consecutive resonant frequency value obtained is closer to the actual resonant frequency of the corona igniter 22 than the previous value obtained. Typically, at the start of each corona event, as shown in FIG. 4, a reduced duty cycle is used and the pulse durations are selected to allow a predefined range of frequencies to be accurately detected. The pulse durations are increased throughout the process of detecting the resonant frequency values while the deadtime durations decrease, as shown in FIGS. 4 and 5, until a maximum pulse duration is achieved. The actual resonant frequency value of the corona igniter 22 is fully identified when the maximum pulse duration is achieved.

For example, the method can include using the first switch 30A to provide the third pulse of energy from the energy supply V3 to the corona igniter 22 for a third pulse duration 103, which is longer than the second pulse duration 102; and ceasing the third pulse duration 103 before the positive current flowing in the corona igniter 22 crosses through zero. No energy is provided to the corona igniter 22 for a third deadtime duration 203 immediately upon ceasing the third pulse duration 103. The third deadtime duration 203 is shorter than the second deadtime duration 202.

The frequency detector then detects when the current flowing in the corona igniter 22 crosses through zero during the third deadtime duration 203. The second switch 30B provides a fourth pulse of energy to the corona igniter 22 at a negative voltage for a fourth pulse duration 104 in response to the zero crossing of the current to cease the third deadtime duration 203. The fourth pulse duration 104 is ceased before the current flowing in the corona igniter 22 crosses through zero. No energy is provided to the corona igniter 22 for a fourth deadtime duration 204 immediately upon ceasing the fourth pulse duration 104.

Next, the frequency detector detects when the current flowing in the corona igniter 22 crosses through zero during the fourth deadtime duration 204, and provides a fifth pulse of energy to the corona igniter 22 at a positive voltage and for a fifth pulse duration 105 in response to the zero crossing of the current to cease the fourth deadtime duration 204. The fourth pulse duration 104 is greater than the third pulse duration 103, and the fourth deadtime duration 204 is less than the third deadtime duration 203.

The frequency detector then obtains a second resonant frequency value based on a sum of the third pulse duration 103, the third deadtime duration 203, the fourth pulse duration 104, and the fourth deadtime duration 204, in the same manner as the first resonant frequency value was obtained. The detected resonant frequency values become more accurate over time, so the second resonant frequency value obtained is typically closer to the actual resonant frequency of the corona igniter 22 than the first resonant frequency value.

As shown in FIGS. 4 and 5, the method typically continues in the same manner, preferably until the actual resonant frequency of the corona igniter 22 is detected, or very close to being detected. A plurality of additional pulses of energy can be provided to the corona igniter 22 after the fifth pulse of energy, wherein each additional pulse of energy is spaced from the next pulse by a deadtime duration during which no energy is provided to the corona igniter 22. The pulse durations continuously increase over time and the deadtime durations continuously decrease over time.

The zero crossings and pulse durations are detected and evaluated to obtain additional resonant frequency values, in the same manner as the first and second resonant frequency values were obtained. Obtaining the additional resonant frequency values is also conducted concurrently with operation of the corona igniter 22, while energy is provided to the corona igniter 22. The controller 28 can also continue to adjust the drive frequency to match the obtained resonant frequency values concurrent with operation of the corona igniter 22 to continuously improve the performance of the system 20. Alternatively, the last resonant frequency value obtained at the end of the resonant frequency detection process, specifically the value based on the last two pulse durations and last two deadtime durations, can be used as the starting drive frequency in a future corona event, or as the drive frequency during a future corona event.

In addition to accurately detect the resonant frequency of the corona igniter 22, the system is also able to make immediate adjustments to the drive frequency, for example in response to resonant frequency changes, in order to maintain the drive frequency equal to, or very close to, the actual resonant frequency of the corona igniter 22. The system 20 is also able to efficiently track and respond to resonant frequency changes caused by arcing events. Quick acquisition of the resonant frequency and rapid real-time adjustment of the drive frequency is possible to maintain the best possible performance. It is also noted that other methods of resonant frequency control which can be employed in the system described herein are disclosed in related U.S. patent application Ser. Nos. 14/568,219, 14/568,330, and 14/568,438, which are incorporated herein by reference. Each application lists the same inventor and was filed on the same day as the present application.

FIG. 1 is a block diagram of the corona discharge ignition system 20 according to a first exemplary embodiment which is capable of implementing the concurrent method for resonant frequency detection of the present invention, and capable of rapidly responding to resonant frequency changes and arc formation concurrent with operation of the corona igniter 22, in order to maintain the drive frequency equal to or approximately equal to the resonant frequency. In addition to the controller 28, switches 30A, 30B, corona igniter 22, induction coil L, and the current sensor 36 described above, the system 20 also includes a pair of drivers 32A, 32B, referred to as a first driver 32A and a second driver 32B. The system 20 of FIG. 1 further includes a transformer 34, a first low-pass filter 38, and a first signal conditioner 40. The voltage provided to the corona igniter 22 and current flowing in the corona igniter 22 is detected at the output 24.

The system 20 is controlled by the controller 28, which is preferably a programmable digital or mixed-signal controller, such as a digital signal processor (DSP), complex programmable logic device (CPLD), field-programmable gate array (FPGA), microcontroller, or microprocessor. The controller 28 receives a trigger input signal 42 which commands the controller 28 to initiate the production of corona discharge 26 in the combustion chamber. The controller 28 also provides an arc detect output signal 44 to inform any external control system (not shown) that an arc has been detected, and a feedback output signal 46 to provide additional data about the health and operation of the circuit to any external control system. The trigger input signal 42, arc detect output signal 44, and feedback output signal 46 conveyed to and from the controller 28 are filtered by electromagnetic capability filters, referred to as EMC filters 48, and other input filters 49. In response to the trigger input signal 42, the controller 28 provides the drive signals 50 to the drivers 32A, 32B which control the switches 30A, 30B. When one of the switches 30A or 30B is active, the energy supply V3, which is a DC voltage, is applied to a primary winding 52 of the transformer 34. The transformer 34 then provides energy through the output 24 and to the corona igniter 22 at the drive frequency. In the exemplary embodiment, the transformer 34 has a configuration known in the art as a "push-pull" configuration.

In the system 20 of FIG. 1, the current flowing in the corona igniter 22 (the output current) is measured at the output 24 by the first current sensor 36. The first current sensor 36 can also collect information about the voltage provided to the corona igniter 22 at the output 24, such as the length of the pulse durations 101, 102, 103, 104 and the deadtime durations 201, 202, 203, 204. The first current sensor 36 can be a shunt resistor, hall-effect sensor, or current transformer, for example. The current sensor 36 identifies the zero crossing of the current during each deadtime duration 201, 202, 203, 204, and sends the output signal 54 including this information toward the controller 28. The first current sensor 36 can use various different techniques to identify the zero crossing. The current sensor can also determine the length of the pulse durations 101, 102, 103, 104 and the length of the deadtime durations 201, 202, 203, 204, and can send this information in the output signal 54.

Preferably, the output signal 54 is lightly filtered by the first low-pass filter 38 before being conveyed to the controller 28. The first low-pass filter 38 creates a phase shift in the output signal 54 which is smaller than the period of oscillation of the current. In one embodiment, the phase shift is 180 degrees, but preferably the phase shift is less than 180 degrees, and more preferably the phase shift is less than 90 degrees, which is less than one half cycle. The first low-pass filter 38 also removes unwanted high frequency noise generated by switching high current and voltages. The filtered output signal 54 is then transferred to the first signal conditioner 40, which makes the output signal 54 safe for transferring to the controller 28. Thus, the output signal 54 is at a level that can be safely handled by the controller 28. The output signal 54 is typically provided to the controller 28 after each zero crossing.

The controller 28 receives the output signal 54 with the current and voltage information obtained by the first current sensor 36, and uses the information to initiate correct timing of the switches 30A, 30B. The length of the first pulse duration 101 is predetermined by the controller 28 before the corona event, but the first deadtime duration 201 is not predetermined. Thus, the controller 28 monitors the current flowing in the corona igniter 22 for the zero crossing via the output signal 54. The zero crossing detection is preferably corrected to account for any delay in measuring the current, delay in the first low-pass filter 38, and the delay in other analogue or digital circuit elements. Immediately upon identifying the zero crossing of the current, the controller 28 terminates the first deadtime duration 201 by activating one of the switches 30A, 30B.

The controller 28 also uses the information contained in the output signal 54 to identify the resonant frequency of the corona igniter 22 concurrent with operation of the corona igniter 22. As discussed above, the controller 28 can use various different techniques to identify the resonant frequency value based on the sum of the pulse durations 101, 102, 103, 104 and the deadtime durations 201, 202, 203, 204. Once the resonant frequency value is obtained, the controller 28 activates the switches 30A, 30B at the correct times so that the drive frequency is equal to that resonant frequency value.

In the exemplary embodiment, once the controller 28 determines the timing of the first switch 30A or second switch 30B required, the controller 28 instructs the first driver 32A to activate the first switch 30A or instructs the second driver 32B to activate the second switch 30B at the required time. The drivers 32A, 32B are instructed to activate the switches 30A, 30B at the predetermined times, so that the drive frequency of the energy conveyed through the switches 30A, 30B to the transformer 34 and ultimately to the corona igniter 22 is equal to the resonant frequency value of the corona igniter 22 obtained by the controller 28. The controller 28 can also adjust the timing of the switches 30A, 30B whenever needed, for example in response to changes of conditions in the system 20, concurrent with operation of the corona igniter 22.

FIG. 2 is a block diagram of a corona discharge 26 ignition system 20 according to a second exemplary embodiment of the invention, which operates like the system 20 of FIG. 1, but includes several additional features. One additional feature is that that the various functional sections of the system 20 include a control system ground 56, a power system ground 58, and load ground 60 which are separated from one another. This technique is used to improve EMI and/or electromagnetic capability (EMC). The control system ground 56 is isolated from a power system ground 58 by galvanic isolation 62. The transformer 34 isolates the power system ground 58 from the load ground 60, and this isolation must be maintained between the first current sensor 36 and the controller 28. The isolation between the power system ground 58 and the load ground 60 may be achieved by adding galvanic isolation 62 at the first low-pass filter 38 or the first signal conditioner 40. Alternatively, the isolation between the power system ground 58 and the load ground 60 can be achieved by operating the first low-pass filter 38 or the first signal conditioner 40 in a differential mode where only a negligible current can flow through the device. In the system 20 of FIG. 2, only the first signal conditioner 40 operates in differential mode to isolate the power system ground 58 from the load ground 60. One or more of these methods may be employed.

Another additional feature of the system 20 of FIG. 2 is a second current sensor 64 to measure the amplitude of the current in the second switch 30B on the primary side of the transformer 34. The second current sensor 64 specifically measures the current at the output of the second switch 30B. Alternatively, there could be a second current sensor 64 at each of the switches 30A, 30B. The second current sensor 64 provides an additional feedback signal 55 to the controller 28, giving valuable diagnostic information which is not possible through the phase measurement of only the first current sensor 36. For example, it is possible to detect an open or short circuit in the load circuit by measuring the current at the output of the switches 30A, 30B. In addition, the system 20 of FIG. 2 includes a second low-pass filter 66 located between the current sensor and the controller 28 to lightly filter the current output signal 54 before providing the feedback signal 55 to the controller 28.

FIG. 3 is a block diagram of a corona discharge 26 ignition system 20 according to a third exemplary embodiment of the invention. The system 20 of FIG. 3 also includes the galvanic isolation 62, but in this embodiment, the galvanic isolation 62 is located on both the energy input and energy output sides of the controller 28, and completely separates the three grounds 56, 58, 60. One or both of the barriers provided by the galvanic isolation 62 can be omitted if the circuit is designed to operate using fewer grounds.

The system 20 of FIG. 3 further includes another winding, referred to as a voltage feedback winding 68. The voltage provided by the voltage feedback winding 68 reflects the voltage at the output 24 of the corona igniter 22. A voltage sensor 78 is preferably located at the output of the voltage feedback winding 68 to measure this voltage. An output signal 80 including the output voltage is then transferred through the second low-pass filter 66 to the controller 28. The second low-pass filter 66 lightly filters the voltage output signal 80 before providing the output signal 80 to the controller 28. The controller 28 can determine the length of the pulse durations 101, 102, 103, 104 and the length of the deadtime durations 201, 202, 203, 204 from the information contained in this output signal 80. Also, unlike the systems 20 of FIGS. 1 and 2, a control signal 72 is provided to the controller 28 of FIG. 3. The control signal 72 can include any information related to operation of the corona igniter 22, such as whether arcing occurred or the desired voltage.

The features of the exemplary systems 20 shown in FIGS. 1-3, as well as those shown in the related applications, may be used in various combinations, other than those specifically described herein. However, the system 20 should have the ability to drive the corona igniter 22 with an AC signal at or near its resonant frequency; enable and disable this AC drive signal; adjust the duty cycle of the voltage supplied to the corona igniter 22 independent of the frequency of the voltage supplied to the corona igniter 22.

The system 20 and method of the present invention provides multiple advantages over comparative systems. As discussed above, the system and method can detect a resonant frequency value that is equal to, or very close to, the actual resonant frequency of the corona igniter 22 concurrent with operation of the corona igniter 22. A complete measurement of the resonant frequency after each cycle can be made, and the measurement can be evaluated and used on a per-cycle basis. Measurement over multiple cycles can also be done to improve the accuracy of the resonant frequency value detected. Immediate adjustments of the drive frequency can be made to maintain the drive frequency at or close to the actual resonant frequency of the corona igniter 22 and thus maintain a robust corona discharge 26.

Obviously, many modifications and variations of the present invention are possible in light of the above teachings and may be practiced otherwise than as specifically described while within the scope of the claims.

What is claimed is:

1. A method for detecting the resonant frequency of a corona igniter in a corona ignition system, comprising the steps of:

providing a first pulse of energy to a corona igniter at a positive voltage for a first pulse duration causing causes current to flow in the corona igniter; ceasing the first pulse duration before the current flowing in the corona igniter crosses through zero and providing no energy to the corona igniter for a first deadtime duration immediately upon ceasing the first pulse duration; detecting when the current flowing in the corona igniter crosses through zero during the first deadtime duration;

providing a second pulse of energy to the corona igniter at a negative voltage for a second pulse duration in response to the zero crossing of the current to cease the first deadtime duration;

ceasing the second pulse duration before the current crosses through zero and providing no energy to the corona igniter for a second deadtime duration immediately upon ceasing the second pulse duration;

detecting when the current flowing in the corona igniter crosses through zero during the second deadtime duration;

providing a third pulse of energy to the corona igniter at a positive voltage in response to the zero crossing of the current to cease the second deadtime duration; and obtaining a first resonant frequency value based on a sum of the first pulse duration, the first deadtime duration, the second pulse duration, and the second deadtime duration.

2. The method of claim 1 including applying energy to the corona igniter at a drive frequency equal to the obtained first resonant frequency value while providing energy to the corona igniter.

3. The method of claim 1, wherein the step of obtaining the first resonant frequency value includes dividing the sum in half to determine the duration of one half cycle of the resonant frequency.

4. The method of claim 1, wherein the positive voltage causes the current to flow in a positive direction and the negative voltage causes the current to flow in a negative direction, and the current crosses zero only once during the first deadtime duration and only once during the second deadtime duration.

5. The method of claim 1, wherein the second pulse duration is greater than the first pulse duration, and the second deadtime duration is less than the first deadtime duration.

6. The method of claim 1 including setting the first pulse duration based on any delays of components of the system so that the step of ceasing the first pulse duration occurs before the current flowing in the corona igniter crosses through zero.

7. The method of claim 1 including adjusting a drive frequency of the energy provided to the corona igniter to match the obtained first resonant frequency value while providing the energy to the corona igniter.

8. The method of claim 1 including providing the third pulse of energy to the corona igniter for a third pulse duration; ceasing the third pulse duration before the current flowing in the corona igniter crosses through zero and providing no energy to the corona igniter for a third deadtime duration immediately upon ceasing the third pulse duration; detecting when the current flowing in the corona igniter crosses through zero during the third deadtime duration;

providing a fourth pulse of energy to the corona igniter at a negative voltage for a fourth pulse duration in response to the zero crossing of the current to cease the third deadtime duration;

ceasing the fourth pulse duration before the current flowing in the corona igniter crosses through zero and providing no energy to the corona igniter for a fourth deadtime duration immediately upon ceasing the fourth pulse duration; detecting when the current flowing in the corona igniter crosses through zero during the fourth deadtime duration;

providing a fifth pulse of energy to the corona igniter at a positive voltage in response to the zero crossing of the current to cease the fourth deadtime duration; and obtaining a second resonant frequency value based on a sum of the third pulse duration, the third deadtime duration, the fourth pulse duration, and the fourth deadtime duration.

9. The method of claim 8, wherein the fourth pulse duration is greater than the third pulse duration and the fourth deadtime duration is less than the third deadtime duration.

10. The method of claim 8 including a plurality of pulses of energy provided to the corona igniter after the fifth pulse of energy, each of the pulses of energy provided for a pulse duration and spaced from one another by a deadtime duration during which no energy is provided to the corona igniter; and wherein the pulse durations increase over time and the deadtime durations decrease over time.

11. The method of claim 8, wherein the steps of obtaining the first resonant frequency value and the second resonant frequency value are conducted while energy is provided to the corona igniter and while the corona igniter provides corona discharge.

12. A method for detecting the resonant frequency of a corona igniter in a corona ignition system, comprising the steps of:

providing a first pulse of energy to a corona igniter at a positive voltage causing causes current to flow in the corona igniter; ceasing the first pulse before the current flowing in the corona igniter crosses through zero and providing no energy to the corona igniter for a first deadtime duration immediately upon ceasing the first pulse of energy; obtaining a first zero crossing duration, wherein the first zero crossing duration begins at the start of the first pulse of energy and ends at the first zero crossing; and obtaining a first resonant frequency value by doubling the first zero crossing duration.

13. A method for detecting the resonant frequency of a corona igniter in a corona ignition system, comprising the steps of:

providing a first pulse of energy to a corona igniter at a positive voltage causing causes current to flow in the corona igniter; ceasing the first pulse before the current flowing in the corona igniter crosses through zero and providing no energy to the corona igniter for a first deadtime duration immediately upon ceasing the first pulse of energy; obtaining a first zero crossing duration, wherein the first zero crossing duration begins at the start of the first pulse of energy and ends at the first zero crossing; providing a second pulse of energy to the corona igniter at a negative voltage in response to the first zero crossing of the current to cease the first deadtime duration; ceasing the second pulse of energy before the current crosses through zero and providing no energy to the corona igniter for a second deadtime duration immediately upon ceasing the second pulse of energy;

obtaining a second zero crossing duration, wherein the second zero crossing duration begins at the first zero crossing and ends at the second zero crossing; and obtaining a first resonant frequency value based on a sum of the first zero crossing duration and the second zero crossing duration.

\* \* \* \* \*